(12) United States Patent
Schertiger et al.

(10) Patent No.: US 9,682,220 B2
(45) Date of Patent: Jun. 20, 2017

(54) ASSEMBLY FOR URINARY DRAINAGE

(75) Inventors: Lars Olav Schertiger, Fredensborg (DK); Helle Haraldsted, Glostrup (DK); Marlene Corydon, Espergaerde (DK)

(73) Assignee: Coloplast A/S, Humlebaek (DK)

( * ) Notice: Subject to any disclaimer, the term of this patent is extended or adjusted under 35 U.S.C. 154(b) by 312 days.

(21) Appl. No.: 14/241,678

(22) PCT Filed: Aug. 28, 2012

(86) PCT No.: PCT/DK2012/050314
§ 371 (c)(1),
(2), (4) Date: Feb. 27, 2014

(87) PCT Pub. No.: WO2013/029622
PCT Pub. Date: Mar. 7, 2013

(65) Prior Publication Data
US 2014/0194842 A1    Jul. 10, 2014

(30) Foreign Application Priority Data

Aug. 29, 2011  (DK) .................................. 2011 70474
Aug. 29, 2011  (DK) .................................. 2011 70475
(Continued)

(51) Int. Cl.
*A61M 25/00* (2006.01)
*A61M 1/00* (2006.01)
(Continued)

(52) U.S. Cl.
CPC ............... *A61M 27/00* (2013.01); *A61F 5/44* (2013.01); *A61F 5/4404* (2013.01);
(Continued)

(58) Field of Classification Search
CPC ..... A61F 5/4404; A61F 5/44; A61M 25/0017; A61M 27/00; A61M 25/002;
(Continued)

(56) References Cited

U.S. PATENT DOCUMENTS 3,871,377 A * 3/1975 Treace ................. A61M 1/0011
604/133
4,161,179 A * 7/1979 Abramson ........... A61M 1/0011
128/DIG. 24
(Continued)

FOREIGN PATENT DOCUMENTS

CN          2928043        8/2007
EP           991701       12/1998
(Continued)

*Primary Examiner* — Adam Marcetich
(74) *Attorney, Agent, or Firm* — Coloplast Corp., Coloplast A/S; Nick Baumann

(57) ABSTRACT

The present invention provides an assembly for urinary drainage. The assembly comprises a urinary drainage device for collecting urine from a body opening and a collecting bag for collecting the urine. The collecting bag comprises a compartment between sheets of a foil material and an inlet into the compartment, which inlet is connected to the device such that a urinary flow can be established in a flow path from the device through the inlet and into the compartment. The collecting bag further comprises a flow promoting element arranged between the sheets and having flow promoting properties. The collecting may also comprise suction means for providing suction through a flow path in the collecting bag.

15 Claims, 7 Drawing Sheets

(30) Foreign Application Priority Data

Aug. 29, 2011  (DK) .................................. 2011 70476
Aug. 29, 2011  (DK) .................................. 2011 70477

(51) Int. Cl.
  *A61F 5/44*  (2006.01)
  *A61M 27/00* (2006.01)

(52) U.S. Cl.
  CPC ........ *A61M 1/0003* (2013.01); *A61M 1/0011* (2013.01); *A61M 1/0015* (2014.02); *A61M 25/0017* (2013.01); *A61M 25/002* (2013.01)

(58) Field of Classification Search
  CPC .......................... A61M 1/0001; A61M 1/0009; A61M 1/0011; A61M 1/0015; A61M 2210/1078; A61M 2210/1085; A61M 2210/1089; A61M 1/0003; Y10S 128/24
  See application file for complete search history.

(56) References Cited

U.S. PATENT DOCUMENTS

| | | | |
|---|---|---|---|
| 4,230,115 A | 10/1980 | Walz | |
| 4,525,166 A * | 6/1985 | Leclerc | A61M 1/0011 604/133 |
| 4,889,533 A | 12/1989 | Beecher | |
| 4,981,474 A * | 1/1991 | Bopp | A61M 1/0011 600/580 |
| 5,001,009 A | 3/1991 | Whitbourne | |
| 5,451,218 A * | 9/1995 | Moore | A61F 5/4404 604/317 |
| 5,928,174 A * | 7/1999 | Gibbins | A61L 15/22 602/41 |
| 2001/0034499 A1* | 10/2001 | Sessions | A61F 13/00021 602/46 |
| 2007/0010797 A1* | 1/2007 | Nishtala | A61B 5/14507 604/540 |
| 2007/0244468 A1* | 10/2007 | Kostandaras | A61M 39/08 604/523 |
| 2008/0103462 A1* | 5/2008 | Wenzel | A61F 13/023 604/313 |
| 2009/0030370 A1* | 1/2009 | Nishtala | A61M 25/0017 604/103.01 |
| 2009/0264840 A1* | 10/2009 | Virginio | A61M 1/0001 604/319 |
| 2009/0292263 A1* | 11/2009 | Hudspeth | A61M 1/0001 604/313 |
| 2011/0202031 A1* | 8/2011 | Mihaylov | G01N 1/10 604/408 |

FOREIGN PATENT DOCUMENTS

| | | |
|---|---|---|
| RU | 2007108204 A | 9/2008 |
| WO | 2011076211 | 6/2011 |

* cited by examiner

ASSEMBLY FOR URINARY DRAINAGE

The present invention relates to an assembly for urinary drainage comprising a urinary drainage device and a collecting bag.

BACKGROUND

Urinary drainage devices for draining the bladder are increasingly used for intermittent as well as indwelling or permanent catheterisation. Typically, urinary draining devices are used by patients suffering from urinary incontinence or by disabled individuals like paraplegics or tetraplegics who have no control permitting voluntary urination and for whom catheterisation is the way of urinating.

Normally, the urine is submitted from the urinary draining device directly into the toilet. However, urinary draining devices exist in combination with bags for collecting the urine. Typically, such collecting bags, however, reduce the free flow of urine and thus increases the duration of drainage of the bladder.

DESCRIPTION OF RELATED ART

CN2928043Y discloses an urination device which is a male portable automatic control urination device, comprising a cover sack, ring gas-bag, suction urine bag, inflating and air-bleed two-way bubble.

U.S. Pat. No. 4,230,115 discloses an aseptic urethral catheterization unit including an elongated initially sealed flexible plastic container sealed at all edges and including a restricted medially disposed opening spaced from one end of the container. An imperforate rupturable means positioned between the restricted opening and the one end of the container to permit ready access to a small chamber formed in said container adjacent to the restricted opening.

SUMMARY OF THE INVENTION

It is an object of embodiments of the present invention to provide an improved assembly for urinary drainage, and particularly, to reduce the duration of drainage of the bladder. The assembly includes a urinary drainage device and a urine collecting bag. Several ways of reducing the duration of drainage of the bladder is disclosed—amongst those, provision of a flow promoting element in the flow path and provision of suction means to provide suction through the flow path. The flow promoting element is able to automatically expand itself from a collapsed to an expanded configuration. The suction means is provided in interaction with the collecting bag itself so that the volume of the collecting bag is increased thereby creating negative pressure. The urinary assembly may also comprise an expansion element.

DETAILED DESCRIPTION OF THE INVENTION

Figures 1A, 1B:
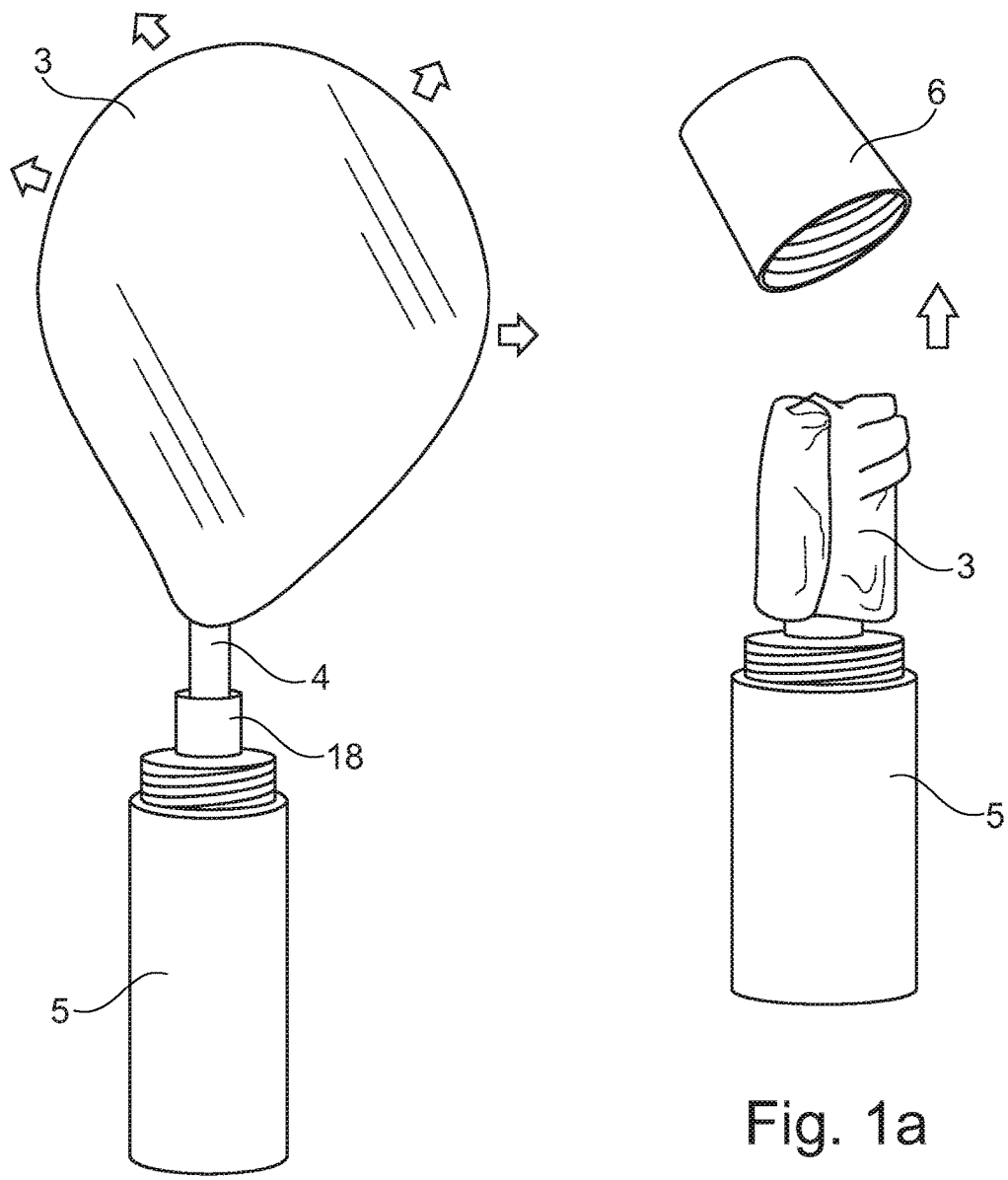
FIGS. 1a and 1b illustrate an assembly for urinary drainage comprising a urinary draining device and a collecting bag.

In a first aspect, the invention provides an assembly for urinary drainage comprising a urinary drainage device for collecting urine from a body opening and a urine collecting bag connected to the device such that a urinary flow can be established in a flow path from the device into the collecting bag, wherein the assembly comprises an expansion element arranged inside the collecting bag.

In an embodiment the urine collecting bag comprises a compartment between sheets of a foil material and an inlet into the compartment, the inlet being connected to the urinary drainage device such that a urinary flow can be established in a flow path from the urinary drainage device through the inlet and into the compartment, wherein the urine collecting bag comprises an expansion element functioning as a flow promoting element arranged between the sheets of the compartment, where the expansion element is able to automatically transform itself from a collapsed configuration to an expanded configuration.

This embodiment has the advantage that the expansion element or flow promoting element in the expanded configuration increases the flow promoting properties.

The expansion element expands when a fluid is provided. This fluid may be in the form of a liquid (e.g. urine or swelling medium) or in the form of air that may be accessible when the assembly is unpacked.

In a second aspect, the invention provides an assembly for urinary drainage comprising a urinary drainage device for collecting urine from a body opening and a collecting bag connected to the device such that a urinary flow can be established in a flow path from the device into the bag, wherein the assembly comprises suction means arranged for providing suction through the flow path into the bag, the suction means being provided by interaction with the collecting bag itself, as the volume of the collecting bag is expanded such that negative pressure is created.

The urine collecting bag may comprise a compartment between sheets of a foil material and an inlet into the compartment. Since sheets may adhere to each other, especially after having been tightly packed in a device package, the free flow of urine may be reduced and the duration of the drainage of the bladder may be increased. In order to reduce the duration of the drainage of the bladder, the collecting bag is according to the first aspect provided with a flow promoting element arranged between the sheets. According to the second aspect, the collecting bag is provided with suction means arranged to provide suction through the flow path into the collecting bag. By reducing the duration of the drainage, the risk of pressure being established in the urethra can be reduced, and the user may thus experience unhindered or at least only limited hindered drainage of the bladder.

In the following, whenever referring to proximal end of an element of the invention, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted.

The longitudinal direction is the direction from the distal to the proximal end. The transverse direction is the direction perpendicular to the longitudinal direction, which corresponds to the direction across the shaft of the catheter.

The urinary draining device may be a standard urinary draining device having well-known dimensions and characteristics. The device could be a catheter or a urisheath or any similar kind of urine collecting device for attachment to or arrangement on the body or in a body cavity.

A catheter comprises a main tubular part extending from the distal end to the proximal end. The tip is positioned in the proximal end of the catheter and is provided as a rounded closed end of the tube constituting the main part of the catheter. The connector is provided in the distal end and may in an embodiment comprise a flared end of the catheter so that the diameter of the connector increases with respect to the tubular part.

Usually catheters used as urinary draining devices are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus 8 FR corresponds to a catheter with an outer diameter of 2.7 mm and 18 FR corresponds to a catheter with an outer diameter of 6 mm.

The catheters used in this invention may prior to use be provided with a hydrophilic coating so as to impart a low-friction insertion.

In one embodiment, the urinary draining device is a telescopic catheter, i.e. the urinary drainage device is connected to the collecting bag by a telescopic tube.

The urine collecting bag may be formed integrally with the urinary draining device. This may especially be an advantage for disabled users, such as paraplegics or tetraplegics, who may have severe difficulties in entering accessible toilets, thus making the use of the assembly for urinary drainage independent of the accessibility of toilets.

It should be understood that the sheets, even though it is expressed in plural, may be formed by one single foil, e.g. a foil which is folded and joined along the edge, or a foil which is shaped like a bag, e.g. by blow-moulding. The sheets could e.g. be the opposing walls of a balloon shaped bag made in one single piece.

The volume of the compartment of the urine collecting bag in a use configuration may be 400-500 ml.

The walls of the urine collecting bag may be coated to facilitate separation of the sheets. It is especially preferred if the coating is in the form of a hydrophilic polymer such as a coating conventionally being used for coating of e.g. catheters for intermittent catherisation. The properties of such coatings are very similar to and considered safe for use in contact with mucosal surfaces and may suitably be those disclosed in U.S. Pat. No. 5,001,009 or European Application No. EP 991701 which will readily adhere to a collecting bag wall made from the materials conventionally used in the art.

The flow promoting properties herein mean that when the expansion element functions as a flow promoting element, it guides the urine, reduces the resistance against a urine flow, or in other ways facilitates urine flow into the urine collecting bag. The flow promoting element thereby reduces the duration of the drainage. Consequently, the risk of pressure being established in the urethra can be reduced and the user may thus experience a more unhindered drainage.

The flow promoting properties reduces flow resistance against a flow of urine into the compartment. This may e.g. be done by expanding the collecting bag by increasing the distance between the sheets forming the compartment. As the volume of the compartment is thereby increased, the flow resistance may be reduced.

The arrangement of the expansion element between the sheets of the urine collecting bag is to be understood as keeping the sheets apart at least in the transition between the urine collecting bag and the urinary drainage device, and particularly to establish a range or volume from the inlet and into the bag where the inner surfaces of the foils are separated. In other words, the expansion element separates the sheets at least at the inlet. As an example, it may be desirable to separate more than 10 percent of the total area of the inner surfaces, or at least 20-30 percent of the total area of the inner surfaces, or the flow promoting element may completely separate the inner surfaces of the bag such that no part of the inner surface is in contact with another part of the inner surface of the bag.

The flow promoting element may be made e.g. from steel, plastic, paper, or synthetic/natural fibres. However, it may be an advantage to use a material which is resistant to urine and/or to whatever liquid or gaseous substance which may be included in the package.

The flow promoting element automatically transforms itself from a collapsed configuration to an expanded configuration, whereby it increases the flow promoting properties. In other words, the flow promoting element possesses shape memory characteristics. By shape memory characteristics should be understood that the flow promoting element will return to its original shape after having been subjected to some form of deformation when between the sheets.

When arranging the flow promoting element between the sheets in a condition where it is deformed away from an initial shape it will tend to return to the initial shape and while doing this expand the bag. Expansion of the flow promoting element may thus increase the flow promoting properties and thereby counteract the reduced free flow which the collecting bag itself may cause. Thus, the flow promoting element may also be seen as an expansion element.

When suction is provided, it is obtained by interaction with the collecting bag itself by expanding the volume of the collecting bag. To facilitate the expansion, the collecting bag may be elastic, such as a balloon, or the collecting bag may be formed of an easy deformable material, e.g. by forming it of two thin-walled sheets. Alternatively or additionally, the collecting bag may include a concertina-folded wall such that the volume can be changed by folding/unfolding that wall. The volume may also be increased by providing an expansion element inside the collecting bag. Thus, an expansion element may be used as a flow promoting element as well as means for providing suction.

It may be an advantage to be able to control the moment of time at which the expansion element expands or the volume increases. To serve this purpose, the assembly may comprise a trigger by which expansion of the expansion element or the volume increase can be initiated. In this way it may be ensured that the urinary draining device is in place and ready to use before the expansion element is expanded or the volume is increased.

In one embodiment a trigger is used to control the expansion element. In another embodiment the trigger is used to increase the volume.

In one embodiment, the trigger can be operated manually, e.g. by pressing a button, pulling a string, unfolding the collecting bag, or by other means releasing the medium used to expand the expansion element or increase the volume. The medium used to expand the expansion element may also be known as expansion medium.

The assembly may further comprise a device package sealingly encapsulating the device and an opening structure for opening the package. In this embodiment, the trigger may be operatively associated with the opening structure such that contact between the expansion medium and the expansion element is automatically initiated upon opening of the device package. Thus, suction through the flow path or promoting of the flow may be provided by opening of the package. Thereby, it may be ensured that the user does not get access to the urinary draining device without releasing the trigger, or at least does not insert the urinary draining device without releasing the trigger.

If the urinary draining device is a telescopic catheter, the trigger may form part of the telescopic mechanism or may be associated with the telescopic mechanism so that the trigger is released when preparing the catheter for use.

In an embodiment of the invention, the expansion element functioning as a flow promoting element transforms itself when the urine collecting bag is transformed from a storage configuration to a use configuration. The transformation from storage to use configuration of the urine collecting bag may correspond to opening of the collecting bag. Suction through the flow path may also be provided when the urine collecting bag is transformed from a storage configuration to a use configuration (or when the collecting bag is opened). In other words, and if a trigger is used, the trigger may be seen as being released, when the collecting bag is transformed from a storage- to a use-configuration. Thus, if a trigger is used, the transformation of the flow promoting element or the provision of suction through the flow path occurs as a result of releasing the trigger. This has the effect that the user will only have to unfold the urine collecting bag—or in other ways prepare the urine collecting bag for use—and then automatically, the flow promoting element will transform itself into the expanded configuration or suction through the flow path will be provided. Users having poor hand-dexterity may find it difficult to release a trigger and in all cases, releasing of a trigger is an extra step that has to be remembered and done. Thereby, the assembly is easy and simple to use.

In the storage configuration, the urine collecting bag may be folded or crumpled to take up as little space as possible. In the use configuration, the urine collecting bag is unfolded to define a compartment for collecting the urine.

To facilitate transformation of the urine collecting bag from the storage configuration to the use configuration, the urine collecting bag may comprise an aperture through which a user may put a finger or more to transform the urine collecting bag. The transformation of the urine collecting bag may be a reshaping or unfolding of the urine collecting bag. Alternatively, the urine collecting bag may comprise a string and transformation or reshaping may take place when pulling this string. As a further alternative, the user may transform or reshape the urine collecting bag and thus release the flow promoting element or provide suction in the flow path by putting his/her elbow on a corner of the bag and then unfold the urine collecting bag away from this corner. Other ways of transforming/reshaping/unfolding the urine collecting bag may also be applicable.

The urinary draining device may be connected to the inlet of the collecting bag via a flexible connection. This connection may comprise slideable connecting means so that the urinary draining device and the collecting bag may slide relative to each other.

In one embodiment, the flow promoting element may be operated from the collapsed configuration to the expanded configuration in response to insertion of at least a part of the urinary draining device through the inlet into the compartment, e.g. when sliding the urinary draining device relative to the collecting bag. The trigger and/or the expansion element itself—e.g. in the form of a spring—may thus be associated to a part of the urinary draining device, so that sliding of the device may initiate suction through the flow path or release of the flow promoting element.

In an embodiment, the expansion element has a flat shape in the collapsed configuration and transforms itself into a three-dimensional shape to define the expanded configuration. The expansion element may also be known as a body of the flow promoting element.

The transformation from a flat shape (a two-dimensional configuration) into a three-dimensional shape will result in an expansion of the volume of the urine collecting bag.

The assembly may be made such that the user receives the assembly with the flat shaped expansion element in an unruptured state. In this state, the flat shaped expansion element may form a closure for preventing a fluid flow in the flow path from the device into the bag. The flat shaped expansion element may thereby prevent liquid and gas, e.g. a liquid swelling medium for rendering a hydrophilic catheter slippery, from escaping through the flow path into the bag.

The suction means may likewise comprise an expansion element arranged in the collecting bag such that expansion of the expansion element causes increase of the volume of the bag and thereby suction through the flow path. The expansion element may as an example be an element which expands automatically when the assembly device is unpacked or alternatively an element which expands when released, e.g. by the user of the assembly device.

The expansion element may be arranged for co-operation with a closed volume which upon expansion creates a negative pressure.

In one embodiment, the expansion element comprises an element with shape memory characteristics. By shape memory characteristics should be understood that the element will return to its original shape after having suffered some form of deformation when arranged for co-operation with the expansion element.

When arranging the element in the collecting bag or in relation to the collecting bag in a condition where it is deformed away from an initial shape it can thus expand the bag upon return to the initial shape. Expansion of the collecting bag may thus provide the required suction through the flow path or promote the flow and thereby counteract the reduced free flow which the collecting bag may cause.

The expansion element may as an example comprise a spring located in the bag. The spring may be any kind of spring, including a disk-spring, a helical-coiled spring, a leaf-spring, etc. If the spring is located in the collecting bag in a compressed condition, the spring will return to an uncompressed condition upon release hereof and thereby suction may be provided in the flow path or the flow may be promoted.

In an alternative embodiment, the expansion element is adapted to expand by contact with an expansion medium. The expansion medium may be gas, liquid, or a hydrophilic material which swells in contact with a swelling medium, e.g. PVP. By contact between the expansion element and the expansion medium the required suction through the flow path or promoting of the flow may be provided.

In another embodiment, the body of the flow promoting element (=the expansion element) is transformed into a helically coiled shape to define the expanded configuration. If the body is located between the sheets of the collecting bag in a collapsed configuration, the body will return to an expanded configuration upon release hereof and thereby more unhindered flow may be provided. Release may be triggered by preparing the collecting bag, e.g. by unfolding it, as the bag may be in a folded configuration in the device package.

To facilitate expansion of the flat shaped body, the flat shaped body may comprise a spiral shaped weakening structure forming a weakening of the material such that the flat shaped body can be ruptured along this spiral shaped weakening structure and thereby form the mentioned helically coiled shape.

In an embodiment, suction may be provided by including a separate membrane arranged about the expansion element, such that the expansion element expands the volume of this separate membrane and thereby provides suction through the flow path.

The expansion element function as a flow promoting element could be in form of one or more springs, spongy bodies, or similar elements which change shape by stretching. Any of such elements could be attached at different locations to the inner surface of the bag and thereby be stretched by reshaping of the bag.

One particular embodiment of an element which changes shape by stretching is herein termed a slit-plate. The slit-plate is a plate shaped element, e.g. a rectangular plate, with two rows of slits, where each slit in one of the rows extends from a first edge of the plate shaped element and more than halfway towards an opposite, second, edge of the plate shaped element. Each slit of the other row of slits extends from the second edge of the plate shaped element and more than halfway towards the first edge of the plate shaped element. The slits in one row of slits are offset from the slits of the other row of slits such that ends of the slits overlay each other. If the slit-plate is stretched by pulling diagonal corners in opposite directions, the slit-plate deforms and becomes capable of separating the sheets of the bag. The slit-plate could be made from paper, cardboard, plastic, metallized foil or any similar material.

Before use, the user may rupture the flat shaped plate along e.g. a weakening line whereby the plate transforms into 3-dimensional shape which separates the inner surfaces of the sheets and due to the rupturing of the flat shaped plate, the flow path opens and urine and other substances can drain into the bag.

To rupture the flat shaped plate along the weakening line, one part of the flat shaped plate could be fixed to one part of the inner surface of the collecting bag, and another part of the flat shaped plate could be fixed to another part of the inner surface of the collecting bag. In this way, the flat shaped plate could be brought from the collapsed to the expanded shape by stretching the bag or in other ways deforming or reshaping the bag.

To ensure a clean and antiseptic assembly or to provide a ready-to-use hydrophilic coated catheter, the assembly may be stored in a device package comprising a container and a cover. The container may be used for storing the urinary draining device, whereas the cover, which may be seen as a lid, may be used for storing the collecting bag. The collecting bag may be tightly folded in the cover to ensure that the size of the device package is as small as possible. It should however be understood, that the urinary draining device and the collecting bag may be an integral unit in the device package. If the device is a hydrophilic catheter, a ready-to-use assembly may be facilitated by providing in the package a liquid medium, e.g. a swelling medium for rendering the coating of the catheter slippery, or an antiseptic solution, a pain relieving solution or any kind of pharmaceutical or non-pharmaceutical medicament. This medium should, however, be present around the urinary drainage device for collecting urine and should therefore be prevented from flowing into the collecting bag. To prevent this flow, the assembly may further comprise a valve for opening of the inlet into the collecting bag. This valve should thus be closed when the assembly is in the device package, e.g. when the assembly is delivered to the user.

Thus, the assembly may further comprise a valve being movable from a closed configuration where the valve prevents a fluid flow through the inlet to an open configuration where the valve allows a fluid flow through the inlet. The valve and the flow promoting element may be operatively connected to enable operation of the valve via the flow promoting element or to enable operation of the flow promoting element via the valve.

The valve and the flow promoting element may be operatively connected to effect automatic operation of the valve upon operation of the flow promoting element or to effect automatic operation of the flow promoting element upon operation of the valve. The valve may also be operatively connected to the trigger. Thereby, it is ensured that the urinary draining device is in place before the flow promoting element is activated and it is prevented that the medium from the container flows into the collecting bag.

A forward end of the flow promoting element may be attached to the collecting bag or to the device in the vicinity of the inlet into the bag. From this position, the flow promoting element may extend into the compartment. In one embodiment, an opposite, rearward, end of the flow promoting element is attached to one or both of the inner surfaces of the sheets which form the bag. This attachment of the rearward end may ensure or at least facilitate a stretched and elongate shape and thus promote a urinary flow far into the bag.

The flow promoting element may be an elongate element with a length dimension being at least 3-15 times a perpendicular width dimension. To ensure a urinary flow deep into the bag and thus to prevent backflow of urine, the length dimension may constitute at least 50 percent, and preferably at least 60-80 percent of the corresponding lengthwise dimension of the bag defined as the longest measurable length from the inlet into the bag.

The flow promoting element may form part of the valve which herein means that the valve and the flow promoting element is in one part and made from a homogenous material.

The assembly may be sterilised by various processes including steam sterilisation and radiation. Since such processes heat up the package and its content, the device package may comprise releasing means for releasing a pressure occurring inside the package during storage or sterilisation. These means may thus ensure that a positive pressure can be neutralised without opening of the package, whereby it may be prevented that a liquid medium present around the urinary device is pressed into the collecting bag. The releasing means may form part of the flow promoting element or suction means.

In a third aspect, the invention provides a method of promoting a fluid flow in an assembly for urinary drainage comprising a urinary drainage device for collecting urine from a body opening and a urine collecting bag with a compartment formed by sheets of a foil material and having an inlet for receiving urine from the urinary drainage device, the method comprising providing a flow promoting element between the sheets, where the flow promoting element automatically expands itself from a collapsed configuration to an expanded configuration in such a way that a fluid flow into the urine collecting bag is promoted.

In a fourth aspect, the invention provides a method of promoting a flow through a urinary drainage device, where the device is connected to a collecting bag in such a way that a flow of urine can be established in a flow path from the device into the bag, the method comprising establishing suction through the flow path into the bag, the suction means being provided by interaction with the collecting bag itself, as the volume of the collecting bag is expanded such that negative pressure is created.

By carrying out the method according to the third or fourth aspect, the user may ensure that a free passage exists through the device and into the collecting bag. Prior to the use of the assembly for urinary drainage, this procedure thereby effectively guarantees that the assembly can be used safely without risk of backflow or other complications which may have been caused by a reduced flow passage or by a completely blocked flow passage.

Accordingly, the invention according to the third or fourth aspect may e.g. be used for indicating correct opening of a valve between the device and the bag, should such a valve exist. For that purpose, the suction may be established in response to opening of the flow path, i.e. upon opening of the valve.

Further, the suction or flow promoting may be applied for the purpose of increasing a flow rate of urine into the bag and thus for facilitating urination. Accordingly, the method may further comprise the step of collecting urine from a body opening of an individual while promoting the flow of urine by the suction.

For detection purposes, i.e. to testify that a correct passage exists, it may be advantageous to control that the pressure drop over the flow path is not too high, and at least not higher than 0.1 bar. For that purpose, the suction may be applied in the range of 0.01-0.1 bar. This pressure drop is also suitable for promoting a urinary flow from the bladder into the bag.

The suction could be provided by compressing a foam material, e.g. by hand, and e.g. while allowing air to escape from the collecting bag and by subsequently allowing the foam material to return to its original shape by absorption of air.

In an embodiment according to the third or fourth aspect, the method includes the step of triggering or releasing a trigger and thereby initiating expansion of the flow promoting element or provision of suction through the flow path. For the user, it may be an advantage to control the moment of expansion of the flow promoting element, because the user can ensure that the assembly is completely ready to use prior to expansion of the flow promoting element. Thus, the user can unpack the assembly and then make the catheter ready without having to handle a large and bulky assembly.

In another embodiment, the flow promoting element transforms itself or suction is initiated when the urine collecting bag is transformed from a storage configuration to a use configuration. Users having poor hand-dexterity may find it difficult to release a trigger and in all cases, releasing of a trigger is an extra step that has to be remembered and done. Thereby, the assembly is easy and simple to use.

DETAILED DESCRIPTION OF THE DRAWING

It should be understood that the detailed description and specific examples, while indicating embodiments of the invention, are given by way of illustration only, since various changes and modifications within the spirit and scope of the invention will become apparent to those skilled in the art from this detailed description.

FIGS. 1a and 1b illustrate an assembly for urinary drainage 1 which comprises a urinary draining device 2 (see FIG. 4) and a collecting bag 3. The urinary drainage device 2 is for collecting urine from a body opening and the urine collecting bag 3 is thus connected to the device such that a urinary flow can be established in a flow path 4 from the device into the bag. The assembly 1 comprises an expansion element or suction means arranged for promoting a fluid flow into the bag 3 or alternatively provide suction through the flow path.

The assembly 1 may prior to its use be stored in a device package comprising a container 5 and a cover 6. The container 5 is used for storing of the urinary draining device 2, whereas the cover 6 which may be seen as a lid is used for storing of the collecting bag 3 in a folded configuration (see FIG. 1a). When detaching the cover 6, the collecting bag 3 can be reshaped into an unfolded configuration (see FIG. 1b).

The collecting bag 3 comprises a compartment between sheets of a foil material. As such sheets may adhere to each other, especially after having been tightly packed in a device package (see e.g. FIG. 1a), the free flow of urine may be reduced and the duration of the drainage of the bladder may be increased.

In order to reduce the duration of the drainage of the bladder, the collecting bag 3 is provided with an expansion element arranged to support the flow into the collecting bag 3. The collecting bag 3 may also be provided with suction means arranged to provide suction through the flow path 4 into the collecting bag 3. By reducing the duration of the drainage, the risk of pressure being established in the urethra can be reduced, and the user may thus experience unhindered or at least only limited hindered drainage of the bladder.

Figure 2:
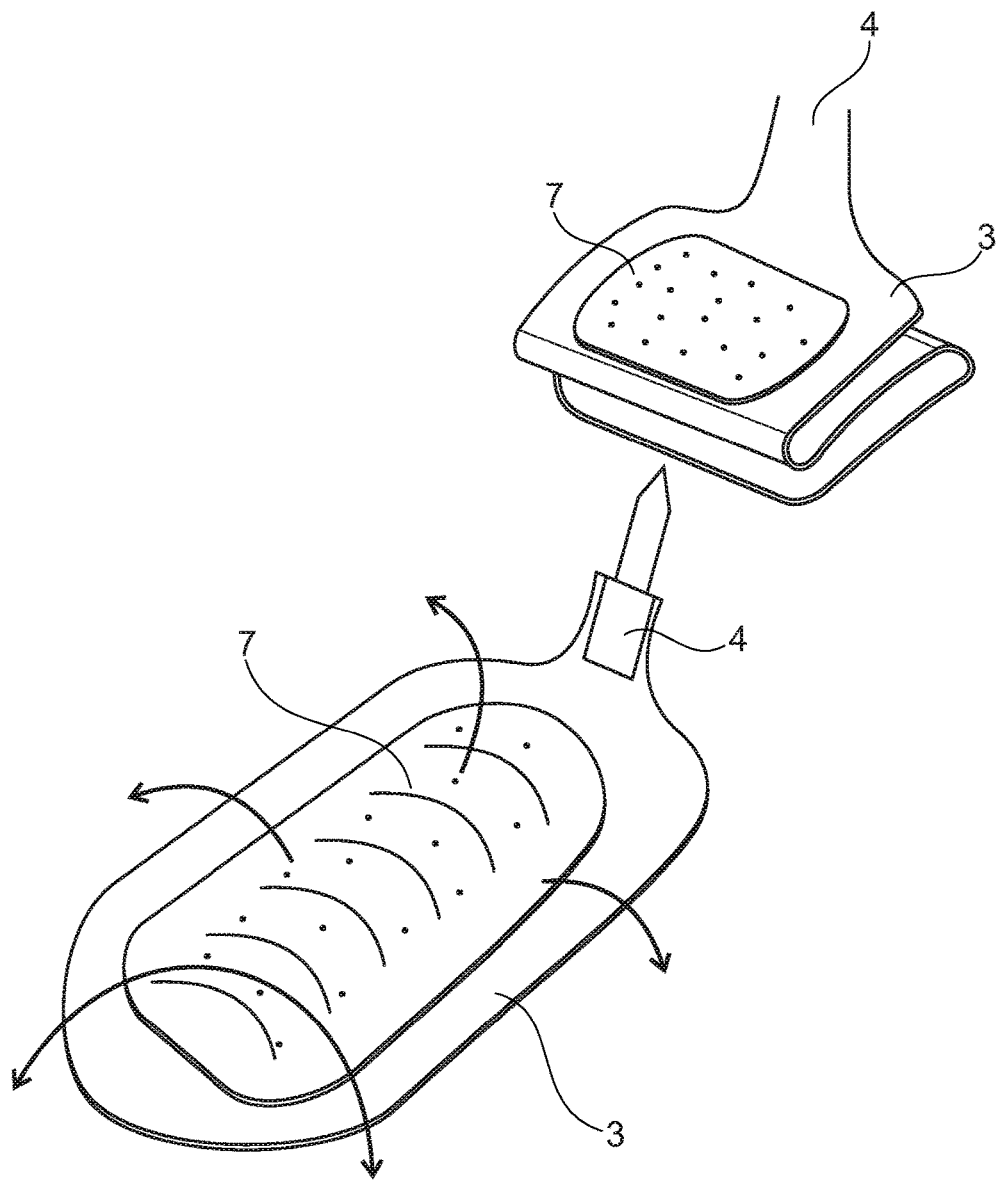
FIG. 2 illustrates the collecting bag in a folded and un-folded configuration.

FIG. 2 illustrates a collecting bag 3 in a folded and un-folded configuration. The bag 3 comprises an expansion element 7 arranged in the collecting bag 3 such that expansion of the expansion element 7 causes expansion of the bag 3 and thereby promotes the flow into the bag or provides suction through the flow path 4. The expansion element 7 of FIG. 2 is a foam material which is adapted to expand by contact with an expansion medium. By contact between the expansion element 7 and the expansion medium, the expansion element 7 expands and thereby separates the sheets of the collecting bag.

Figure 3:
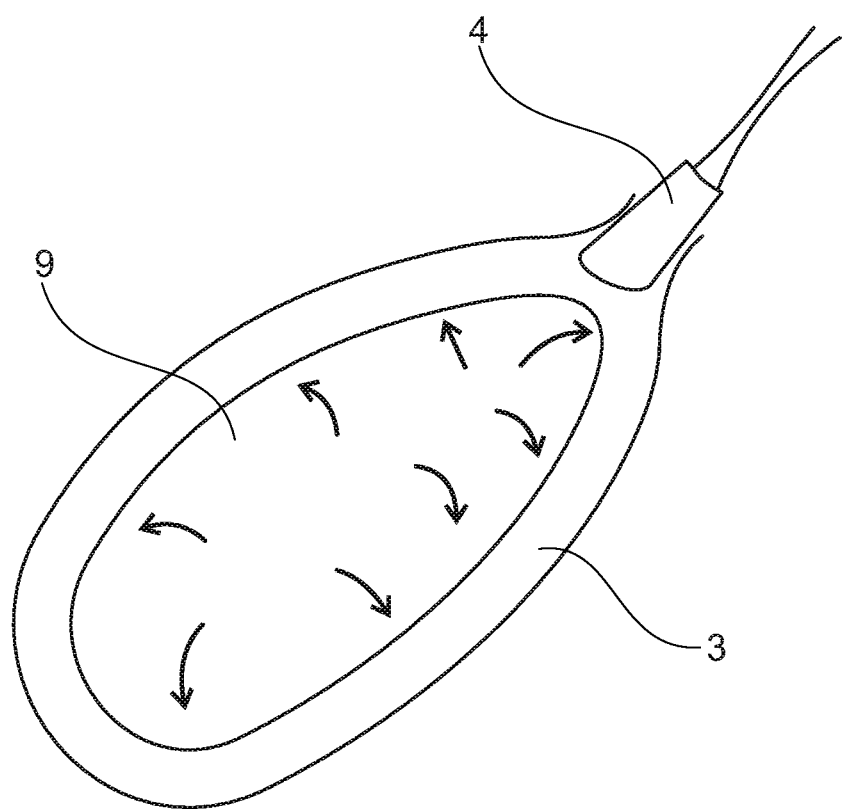
FIG. 3 illustrates the collecting bag comprising an expansion element.

In FIG. 3 an alternative embodiment of an expansion element 9 is illustrated. The expansion element 9 comprises a foam material which may be compressed by the user of the assembly 1 by squeezing it by hand. When releasing the expansion element 9 again it will promote the flow or provide suction through the flow path 4 as it will return to its original shape by absorption of air which then creates the suction.

Figure 4C:
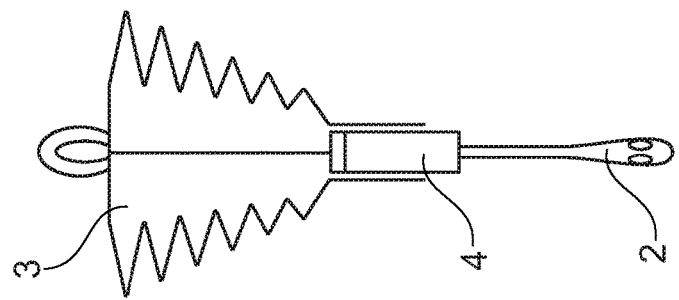
FIGS. 4a-4c illustrate different embodiments of a concertina-shaped collecting bag.
Figure 4B:
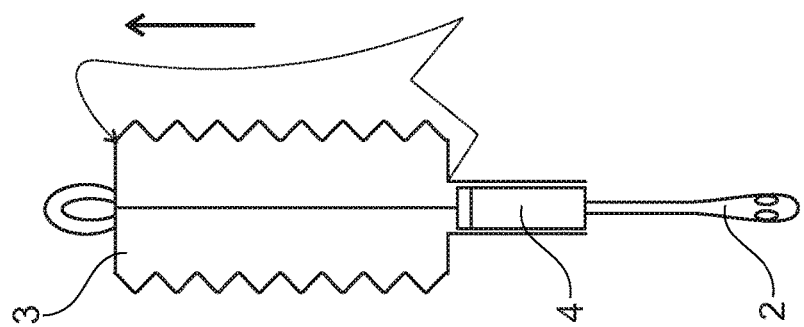
Figure 4A:
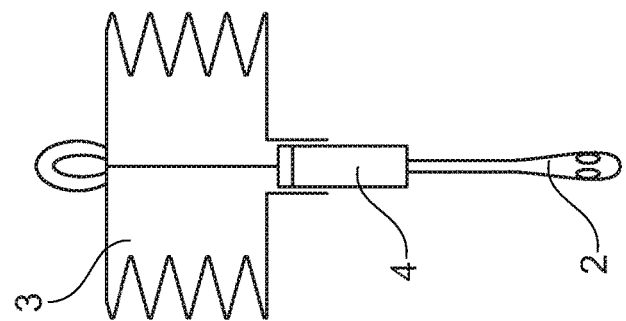

FIGS. 4a and 4c illustrate two different embodiments of a concertina-shaped collecting bag 3. Before use the collecting bag 3 is in a folded configuration in which the bag is compressed (see FIG. 4a). When unfolding the collecting bag 3 (see FIG. 4b), suction is provided through the flow path 4. The embodiment of FIG. 4c is similar to the embodiment of FIGS. 4a and 4b with the exception of the form of the collecting bag 3 which in FIG. 4c tapered down towards the flow path 4. The operation of the embodiment is however identical.

Figure 5A:
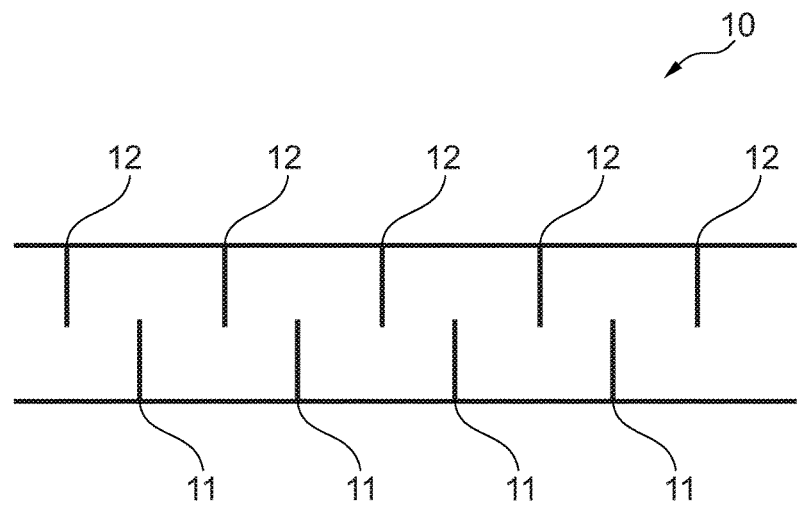
FIG. 5a illustrates an embodiment of an expansion element.

FIG. 5a illustrates an embodiment of an expansion element 10 in the form of a rectangular slit-plate with two rows of slits 11, 12. Slits 11 of a first row of slits extend from a first edge of the plate shaped element 10 and more than halfway towards an opposite, second, edge of the plate shaped element. Slits 12 of a second row of slits extend from the second edge of the plate shaped element 10 and more than halfway towards the first edge of the plate shaped element in such a way that the first row of slits 11 are offset from the slits 12 of the second row of slits. FIG. 5a illustrates that the ends of the slits 11 of the first group of slits overlay the ends of the slits 12 of the second group of slits. If the slit-plate 10 is stretched by pulling diagonal corners in opposite directions, the slit-plate 10 deforms and becomes capable of separating the sheets of the bag 3. The slit-plate 10 could be made from paper, cardboard, plastic, metallized foil or any similar material.

Figure 5B:
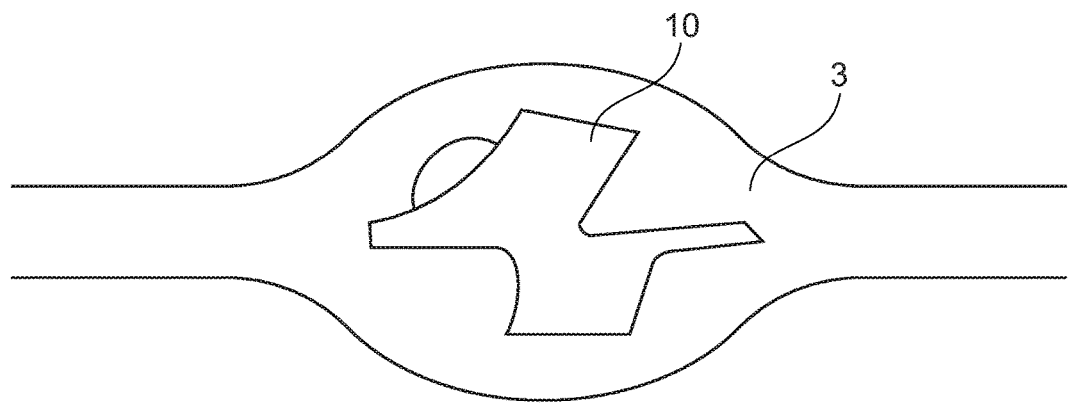
FIG. 5b illustrates a collecting bag comprising the expansion element of FIG. 5a in an expanded configuration.

FIG. 5b illustrates a collecting bag 3 comprising the slit-plate 10 of FIG. 5a in an expanded configuration.

Figure 6A:
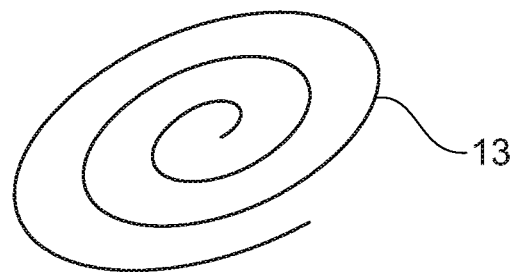
FIGS. 6a and 6b illustrate an embodiment of an expansion element in a compressed configuration and in an expanded configuration.
Figure 6B:
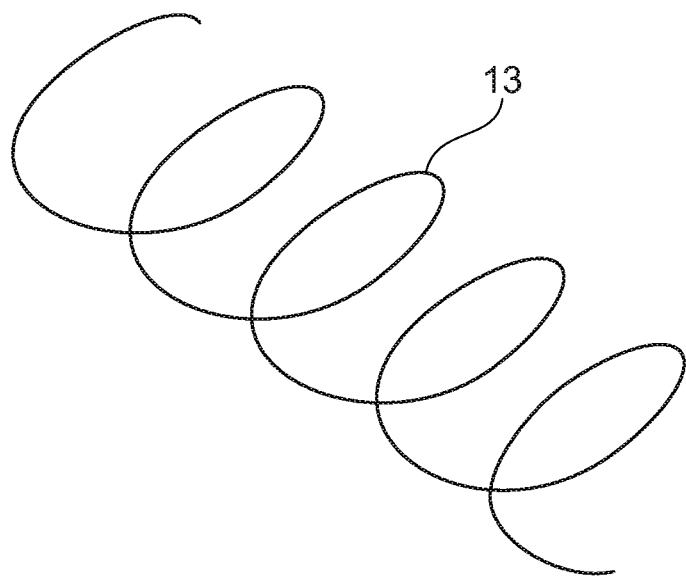

FIGS. 6a and 6b illustrate an embodiment of an expansion element 13 in the form of a spring in a compressed configuration and in an expanded configuration.

Figure 7:
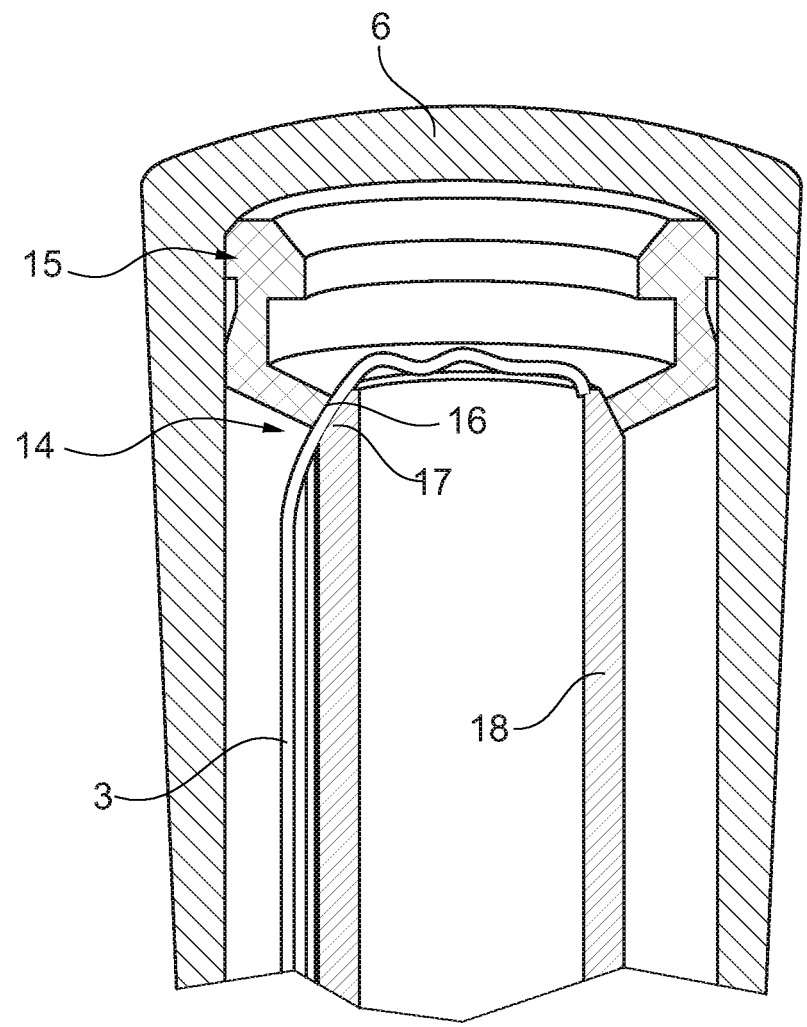
FIG. 7 illustrates an embodiment of an assembly comprising a valve.

FIG. 7 illustrates an embodiment of an assembly 1 comprising a valve 14. The valve 14 is formed by an elastic valve seal 15 which is attached to the inside of the cover 6. The valve seal 15 can for example be formed of silicone or other elastomeric materials. The valve seal 15 has a valve seat 16 which engages with a handle seat 17 on the distal part of the handle 18 when the device package is closed. The handle 18 could typically be the connector part of a catheter which is located opposite the insertable tip end of the catheter.

The collecting bag 3 which is attached to the handle 18 extends between the valve seat 16 and the handle seat 17. However, due to the pressure between the two seats 16, 17, the collecting bag 3 is compressed and liquid flow is prevented across the valve seal 15.

When the cover 6 is removed, the seal 15 is broken and suction can be provided or flow may be promoted through the flow path 4. However, if the cover 6 is returned, the valve seat 16 will re-establish contact with the handle seat 17, thereby preventing flow.

The invention claimed is:

1. An assembly for urinary drainage comprising:
   a urinary drainage device for collecting urine from a body opening;
   a urine collecting bag connected to the urinary drainage device;
   an expansion element disposed inside of the urine collecting bag; and
   a trigger operable to expand the expansion element;
   wherein the expansion element is a slit-plate comprising a plate shaped element with at least two rows of slits, where slits of a first row of slits extend from a first edge of the plate shaped element to more than halfway towards an opposite, second, edge of the plate shaped element, where slits of a second row of slits extend from the second edge of the plate shaped element to more than halfway towards the first edge of the plate shaped element, and where the slits in the first row of slits are offset from the slits of the second row of slits.

2. An assembly according to claim 1, wherein the urinary drainage device is a telescopic catheter.

3. An assembly according to claim 2, wherein the trigger is coupled to a telescopic mechanism of the telescopic catheter.

4. An assembly according to claim 1, wherein the trigger is operated manually.

5. An assembly according to claim 1, wherein the urinary drainage device is connected to an inlet of the urine collecting bag by a slidable connecting element.

6. An assembly according to claim 1, wherein the expansion element is a shape memory element.

7. An assembly according to claim 1, wherein the slit-plate comprises a weakening line.

8. An assembly according to claim 1, wherein the trigger is a string connected to the expansion element.

9. An assembly according to claim 1, wherein the urine collecting bag is elastic.

10. An assembly according to claim 1, wherein the urine collecting bag is a concertina folded urine collecting bag.

11. An assembly configured to collect urine, the assembly comprising:
    a urinary catheter;
    a urine collecting bag connected to the urinary catheter; and
    an expansion plate disposed inside of the urine collecting bag, the expansion plate including a plurality of slit openings formed through a thickness of the plate,
    wherein the plurality of slit openings includes a first row of openings, with each opening extending from a first edge of the expansion plate a distance of more than halfway towards an opposite, second edge of the expansion plate.

12. The assembly of claim 11, wherein the plurality of slit openings includes the first row of slit openings spaced apart and offset from a second row of slit openings.

13. The assembly of claim 11, wherein the expansion plate is configured to expand from a first thickness to a second expanded thickness that is larger than the first thickness.

14. The assembly of claim 11, wherein the expansion plate is fabricated from one of paper, plastic, cardboard, and metalized foil.

15. The assembly of claim 11, wherein the plurality of slit openings includes a second row of openings, with each opening extending from the second edge of the expansion plate a distance of more than halfway towards the first edge of the expansion plate.

* * * * *